United States Patent
Mukherjee et al.

(10) Patent No.: US 11,492,307 B2
(45) Date of Patent: Nov. 8, 2022

(54) PROCESS OF MAKING OLEFINS OR ALKYLATE BY REACTION OF METHANOL AND/OR DME OR BY REACTION OF METHANOL AND/OR DME AND BUTANE

(71) Applicant: Exelus Inc., Fairfield, NJ (US)

(72) Inventors: Mitrajit Mukherjee, Livingston, NJ (US); Vamsi M. Vadhri, Kearny, NJ (US); Narendra Joshi, Jersey City, NJ (US)

(73) Assignee: Exelus Inc., Fairfield, NJ (US)

( * ) Notice: Subject to any disclaimer, the term of this patent is extended or adjusted under 35 U.S.C. 154(b) by 0 days.

(21) Appl. No.: 16/867,487

(22) Filed: May 5, 2020

(65) Prior Publication Data
US 2020/0283354 A1  Sep. 10, 2020

Related U.S. Application Data

(62) Division of application No. 16/246,462, filed on Jan. 12, 2019, now Pat. No. 10,662,126, which is a (Continued)

(51) Int. Cl.
*C07C 2/86* (2006.01)
*C07C 2/58* (2006.01)
(Continued)

(52) U.S. Cl.
CPC ............ *C07C 2/864* (2013.01); *B01J 8/04* (2013.01); *B01J 21/04* (2013.01); *B01J 21/08* (2013.01);
(Continued)

(58) Field of Classification Search
CPC .. C07C 2/864; C07C 1/20; C07C 2/58; C07C 2/865; C07C 5/373; C07C 2521/04;
(Continued)

(56) References Cited

U.S. PATENT DOCUMENTS 3,702,886 A    11/1972  Argauer et al.
3,709,979 A     1/1973  Chu
(Continued)

FOREIGN PATENT DOCUMENTS

CN    103130604 A    6/2013
CN    103447078 B    8/2015

OTHER PUBLICATIONS

Machine Translation of Description of CN103447078B.
(Continued)

*Primary Examiner* — Thuan D Dang
(74) *Attorney, Agent, or Firm* — Frank Rosenberg

(57) ABSTRACT

Methods of simultaneously converting butanes and methanol to olefins over Ti-containing zeolite catalysts are described. The exothermicity of the alcohols to olefins reaction is matched by endothermicity of dehydrogenation reaction of butane(s) to light olefins resulting in a thermoneutral process. The Ti-containing zeolites provide excellent selectivity to light olefins as well as exceptionally high hydrothermal stability. The coupled reaction may advantageously be conducted in a staged reactor with methanol/DME conversion zones alternating with zones for butane(s) dehydrogenation. The resulting light olefins can then be reacted with iso-butane to produce high-octane alkylate. The net result is a highly efficient and low cost method for converting methanol and butanes to alkylate.

13 Claims, 5 Drawing Sheets

Related U.S. Application Data division of application No. 15/331,727, filed on Oct. 21, 2016, now Pat. No. 10,179,753.

(60) Provisional application No. 62/244,677, filed on Oct. 21, 2015.

(51) Int. Cl.

| | |
|---|---|
| B01J 29/89 | (2006.01) |
| B01J 23/80 | (2006.01) |
| B01J 29/70 | (2006.01) |
| B01J 29/40 | (2006.01) |
| B01J 21/04 | (2006.01) |
| B01J 21/08 | (2006.01) |
| B01J 29/18 | (2006.01) |
| B01J 29/08 | (2006.01) |
| B01J 35/10 | (2006.01) |
| B01J 8/04 | (2006.01) |
| C07C 1/20 | (2006.01) |
| C07C 5/373 | (2006.01) |
| C10G 29/20 | (2006.01) |
| C10G 3/00 | (2006.01) |
| B01J 21/12 | (2006.01) |
| B01J 35/02 | (2006.01) |

(52) U.S. Cl.
CPC ............. B01J 21/12 (2013.01); B01J 23/80 (2013.01); B01J 29/08 (2013.01); B01J 29/087 (2013.01); B01J 29/18 (2013.01); B01J 29/40 (2013.01); B01J 29/7007 (2013.01); B01J 29/7057 (2013.01); B01J 29/89 (2013.01); B01J 35/023 (2013.01); B01J 35/1019 (2013.01); B01J 35/1023 (2013.01); B01J 35/1057 (2013.01); C07C 1/20 (2013.01); C07C 2/58 (2013.01); C07C 2/865 (2013.01); C07C 5/373 (2013.01); C10G 3/49 (2013.01); C10G 29/205 (2013.01); B01J 2523/00 (2013.01); C07C 2521/04 (2013.01); C07C 2521/06 (2013.01); C07C 2521/08 (2013.01); C07C 2521/12 (2013.01); C07C 2523/755 (2013.01); C07C 2523/80 (2013.01); C07C 2529/08 (2013.01); C07C 2529/18 (2013.01); C07C 2529/40 (2013.01); C07C 2529/89 (2013.01)

(58) Field of Classification Search
CPC ............ C07C 2521/06; C07C 2521/08; C07C 2521/12; C07C 2523/755; C07C 2523/80; C07C 2529/08; C07C 2529/18; C07C 2529/40; C07C 2529/89; C07C 9/21; B01J 8/04; B01J 21/04; B01J 21/08; B01J 21/12; B01J 23/80; B01J 29/08; B01J 29/087; B01J 29/18; B01J 29/40; B01J 29/7007; B01J 29/7057; B01J 29/89; B01J 35/023; B01J 35/1019; B01J 35/1023; B01J 35/1057; B01J 2523/00; B01J 23/42; B01J 23/96; B01J 27/10; B01J 29/90; B01J 2219/00033; C10G 3/49; C10G 29/205; Y02P 30/20; Y02P 30/40

See application file for complete search history.

(56) References Cited

U.S. PATENT DOCUMENTS

| | | |
|---|---|---|
| 3,832,449 A | 8/1974 | Rosinski et al. |
| 3,894,107 A | 7/1975 | Butter et al. |
| 3,911,041 A | 10/1975 | Kaeding et al. |
| 3,931,349 A | 1/1976 | Kuo |
| 3,969,426 A | 7/1976 | Owen et al. |
| 4,025,571 A | 5/1977 | Lago |
| 4,025,575 A | 5/1977 | Chang et al. |
| 4,025,576 A | 5/1977 | Chang et al. |
| 4,046,825 A | 9/1977 | Owen et al. |
| 4,049,573 A | 9/1977 | Kaeding |
| 4,052,479 A | 10/1977 | Chang et al. |
| 4,059,646 A | 11/1977 | Wald et al. |
| 4,059,647 A | 11/1977 | Wald et al. |
| 4,062,905 A | 12/1977 | Chang et al. |
| 4,067,827 A | 1/1978 | Takano et al. |
| 4,079,095 A | 3/1978 | Givens et al. |
| 4,079,096 A | 3/1978 | Givens et al. |
| 4,088,706 A | 5/1978 | Kaeding et al. |
| 4,126,642 A | 11/1978 | Kim et al. |
| 4,387,261 A | 6/1983 | Chester et al. |
| 4,387,263 A | 6/1983 | Vogt et al. |
| 4,410,501 A | 10/1983 | Taramasso et al. |
| 4,465,889 A * | 8/1984 | Anthony .................. C07C 1/20 502/239 |
| 4,499,314 A | 2/1985 | Seddon et al. |
| 4,587,373 A | 5/1986 | Hsia |
| 4,627,911 A | 12/1986 | Chen et al. |
| 4,677,242 A | 6/1987 | Kaiser |
| 4,746,761 A | 5/1988 | Avidan et al. |
| 4,985,203 A | 1/1991 | Tabak |
| 5,095,163 A | 3/1992 | Barger |
| 5,126,308 A | 6/1992 | Barger et al. |
| 5,191,141 A | 3/1993 | Barger et al. |
| 5,346,871 A * | 9/1994 | Robbins .................. C07C 5/325 502/238 |
| 6,316,683 B1 | 11/2001 | Janssen et al. |
| 6,403,854 B1 | 6/2002 | Miller et al. |
| 6,613,951 B1 | 9/2003 | Brown et al. |
| 7,148,172 B2 | 12/2006 | Stromaier et al. |
| 7,825,287 B2 | 11/2010 | Ahn et al. |
| 9,035,120 B2 | 5/2015 | Nesterenko et al. |
| 2006/0020155 A1 | 1/2006 | Beech et al. |
| 2011/0124934 A1 | 5/2011 | Bulut et al. |
| 2012/0053378 A1 | 3/2012 | O'Rear |
| 2014/0005455 A1 | 1/2014 | Spannhoff et al. |
| 2014/0051900 A1 | 2/2014 | Liu |
| 2014/0357912 A1 | 12/2014 | Mandal et al. |
| 2017/0022126 A1 | 1/2017 | Mukherjee |

OTHER PUBLICATIONS

Machine Translation of Description of CN103130604A.
European Search Opinion and Extended European Search Report from European Patent Application EP 20171075.3, dated Aug. 20, 2020.
1st Office Action from Chinese Patent Application CN201680067393.5, dated Aug. 27, 2020.
Translation of 1st Office Action from Chinese Patent Application CN 201680067393.5, dated Aug. 27, 2020.
2nd Office Action from Chinese Patent Application CN 201680067393.5, dated Nov. 24, 2021.
Translation of 2nd Office Action from Chinese Patent Application CN 201680067393.5, dated Nov. 24, 2021.
Mier et al., "Catalyst discrimination for olefin production by coupled methanol/n-butane cracking", Applied Catalysis A: General 383 (2010) 202-210, Elsevier B.V.
Roohollahi et al., "The joint reaction of methanol and i-butane over the HZSM-5 zeolite", Journal of Industrial and Engineering Chemistry 19 (2013) 915-919, Elsevier B.V.
Hajheidary et al., "Olefins production from LPG via dehydrogenative cracking over three ZSM-5 catalysts", Journal of Scientific & Industrial Research, 2013, vol. 72, pp. 760-766.
Lu, et al., "FeHZSM-5 molecular sieves—Highly active catalysts for catalytic cracking of isobutane to produce ethylene and propylene", Catalysis Communications, 2006, vol. 7, pp. 199-203, Elsevier B.V.
Lücke et al., "CMHC: coupled methanol hydrocarbon cracking: Formation of lower olefins from methanol and hydrocarbons over modified zeolites", Microporous and Mesoporous Materials, 1999, vol. 29, pp. 145-157, Elsevier.

(56) References Cited

OTHER PUBLICATIONS

Martin et al., "Coupled Conversion of Methanol and C4 Hydrocarbons to Lower Olefins", Applied Catalysis, 1989, vol. 50, pp. 149-155, Elsevier Science Publishers B.V., Amsterdam.
Mier et al. "Catalyst discrimination for olefin production by coupled methanol/n-butane cracking", Applied Catalysis A: General, 2010, vol. 383, pp. 202-210, Elsevier B.V.
Serrano et al."Turning TS-1 zeolite into a highly active catalyst for olefin epoxidation with organic hydroperoxides", Chem. Commun., 2009, pp. 1407-1409, The Royal Society of Chemistry, Cambridge, United Kingdom.
Silvestre-Albero et al., "Desilication of TS-1 zeolite for the oxidation of bulky molecules", Catalysis Communications, 2014, vol. 44, pp. 35-39, Elsevier B.V.
Song et al. "Effect of cofeeding n-butane with methanol on aromatization performance and coke formation over a Zn loaded ZSM-5/ZSM-11 zeolite", Applied Catalysis A: General, 2014, vol. 470, pp. 15-23, Elsevier B.V.
International Preliminary Report on Patentability from International Application No. PCT/US2016/038827, dated Dec. 26, 2017.
Office Action with embedded translation from Indian Application No. IN 201837017119, dated Mar. 3, 2020.

\* cited by examiner

PROCESS OF MAKING OLEFINS OR ALKYLATE BY REACTION OF METHANOL AND/OR DME OR BY REACTION OF METHANOL AND/OR DME AND BUTANE

This is a divisional of U.S. patent application Ser. No. 16/246,462 filed Jan. 12, 2019 which was a divisional of U.S. patent application Ser. No. 15/331,727 filed Oct. 21, 2017, now U.S. Pat. No. 10,179,753 which claims the benefit of U.S. Provisional Patent Application No. 62/244, 677 filed Oct. 21, 2016.

INTRODUCTION

The US is currently undergoing a quiet revolution in fossil energy. Recent technological advances, specifically the confluence of horizontal drilling and hydraulic fracturing, have enabled vast gas reserves locked in shale formations to be cost effectively tapped for the first time. The ability to access these resources has led to a sudden decoupling of the traditional link between petroleum and natural gas prices. Converting methane (the largest component of natural gas) to methanol is a well-established method for monetizing methane. Methanol is one of the most widely-produced chemicals in the world. It is a key raw material in the production of many chemicals in the petrochemical industry. Shale gas now constitutes about 20% of the national gas supply, and is rising rapidly. As a result, the use of natural gas in the world energy market is growing faster than that of any other fossil fuel and will continue to increase over the next two decades.

While methanol is often touted as a fuel of the future due to the ease with which it is synthesized from a variety of feedstocks, it is fraught with several issues. Methanol (19.7 MJ/kg) has a much lower energy density than conventional transportation fuels (~46 MJ/kg). Furthermore, methanol is difficult to use directly as a fuel because it is highly hygroscopic and results in corrosion where it is used. Widespread use of methanol as a transportation fuel would require development of effective methods for distribution and more robust end-use systems (engines). Methanol is already used today on a large scale as a raw material to produce a variety of chemicals and products. Through the methanol-to-gasoline (MTG) process, it can be transformed into gasoline and aromatics. Using the methanol-to-olefin (MTO) process, methanol can also be converted to ethylene and propylene, the two largest chemicals produced by the petrochemical industry.

It is generally accepted that the methanol to hydrocarbon reaction mechanism occurs via a mechanism known as the hydrocarbon pool mechanism. There are two cycles, one in which olefins are methylated to form larger species susceptible to cracking. In the other cycle aromatic species are repeatedly methylated and dealkylated to form light olefins The major chemistries involved in this process are (a) olefin methylation, (b) olefin cracking, (c) hydrogen transfer, (d) cyclization, (e) aromatic methylation, and (f) aromatic dealkylation.

Existing catalysts for the MTG and MTO processes are ZSM-5 and SAPO-34 respectively. ZSM-5 is a highly acidic, medium-pore zeolite that produces a plethora of products including gasoline-grade isoparaffins, aromatics, and light hydrocarbons. This poor selectivity results in fuel-additive with up to 30 vol % aromatics.

SAPO catalysts have much smaller pores (4.3 Å) which is smaller than that of benzene (5.8 Å) and other aromatic compounds. Therefore, it only allows diffusion of light compounds (olefins) out of the crystalline structure. This also means that it has a rapid build-up of aromatic compounds which coke the catalyst. MTO processes using SAPO require complicated fluidized bed reactors with catalyst regeneration loops.

The reaction sequence begins with light olefins and chain growth occurs via methylation and, eventually, cyclization. Light olefins are produced early in the reaction sequence and by cracking of heavier hydrocarbons

PRIOR ART

Many catalytic materials have been investigated for the conversion of oxygenates to hydrocarbon fuels and/or light olefins. Microporous crystalline materials like ordered aluminosilicates (such as ZSM-5, chabazite or aluminosilicates) or silicoaluminophosphates (such as SAPO-34 or SAPO-18) have been favored for these reactions mostly because of tunable acid and morphological properties.

While methanol-to-gasoline (MTG) and methanol-to-olefins (MTO) have been the major pathways for the conversion of methanol to hydrocarbons, other paths have also been discussed in literature. U.S. Pat. Nos. 4,059,646; 4,059,647; 4,126,642; 7,825,287 B2 disclose a method for the direct conversion of methanol and/or dimethylether to high octane iso-C7 molecules (triptane or triptene) at relatively low temperatures (less than 300° C.). The process can also include alkanes in the feed which can react with DME and/or methanol. Catalysts used primarily in this process are H-Beta (though other catalysts like H-Mordenite and H-FAU have been tested). Overall hydrocarbon selectivities to C7 molecules have been reported to be between 20-30 wt % of which the iso-C7 molecule fraction was over 80 wt %.

Methanol to Gasoline (MTG):

The MTG process, announced by Mobil in 1976, converts methanol and/or dimethylether directly into gasoline range drop-in fuel. Typically, aluminosilicate zeolites have been used as catalysts. Specifically, the catalysts which have been shown to be effective are ZSM-5, ZSM-11, ZSM-12, ZSM-21 and TEA-Mordenite (disclosed in U.S. Pat. Nos. 3,702, 886, 3,709,979, 3,911,041, 4,025, 571, 4,025,575, and 4,052,479).

However, the MTG process suffers from serious drawbacks—

1. Generation of large amounts of heat—Roughly 1.74 MJ/kg of methanol reacted is released with the adiabatic temperature rising to 600° C. Various strategies such as a large amount of recycle or a fluidized bed reactor have been proposed to manage excessive heat. U.S. Pat. No. 3,931,349 discloses the use of a hydrocarbon diluent to dissipate exothermic heat in a two-stage conversion of methanol to gasoline.
2. Formation of durene (1,2,4,5-tetramethylbenzene). Durene is the largest compound formed in a significant way from the methanol-to-gasoline reaction. It is believed to form as a result of the reaction between the unconverted methanol and the aromatic molecules. While it has a high octane number, it is solid at room temperature (melting point 79 C). This might cause it to fractionate out of the liquid fuel and cause driveability problems. Methods have been suggested to curb the formation of durene. These include—
   a. first converting methanol to olefins and the converting the olefins to gasoline range compounds in a separate reactor (disclosed in U.S. Pat. No. 4,025,576) or
   b. performing post reaction treatment of durene by transalkylating it with a mixture of benzene and toluene (disclosed in U.S. Pat. Nos. 4,067,827; 3,969,426), dealkylating it over an acid catalyst (disclosed in U.S. Pat. No. 4,387,261) or hydrotreating it over a Pt/ZSM catalyst (disclosed in U.S. Pat. No. 3,832,449).

3. Formation of low molecular weight paraffins—Since these molecules cannot be used as a liquid fuel due to their high volatility, they have to be used as low-cost fuel gas or LPG.

US. Pat. No. 2012/0053378 discloses a method to produce gasoline range compounds from methanol using a three-stage reacting system. The methanol stream is split into two streams—one stream is converted to a mixture of paraffins and gasoline range compounds using conventional MTG technology and the other stream is converted to a mixture of olefins using a MTO catalyst. At least a portion of the products from the two streams are reacted using ionic liquids as an alkylation catalyst to obtain high octane gasoline range products.

Methanol to Olefins (MTO):

Another proposed way to synthesize chemical products from methanol and its derivatives to useful products is to catalytically convert them to a mixture of olefins over crystalline aluminosilicates or silicoaluminophosphates.

Use of crystalline aluminosilicate zeolites for the MTO process is disclosed in U.S. Pat. Nos. 3,894,107; 4,046,825; 4,062,905; 4,079,095; 4,079,096; 3,911,041; and 4,049,573. U.S. Pat. No. 3,911,041 discloses converting methanol to olefins over a catalyst such as ZSM-5 containing phosphorus incorporated into the crystal structure of the zeolite. U.S. Pat. No. 4,088,706 discloses converting methanol to light olefins and aromatics over a crystalline aluminosilicate catalyst modified by the addition of boron oxide or magnesium oxide. U.S. Pat. No. 4,062,905 discloses a process for the conversion of methanol and/or dimethylether to a mixture of ethylene rich hydrocarbons over a silicoaluminate catalyst with a pore size less than 6 A and comprising an 8 membered oxygen atom ring. U.S. Pat. No. 4,387,263 discloses a method where methanol was converted to hydrocarbons over a ZSM-5-type of catalyst system. While high yields of ethylene and propylene were reported, there was a significant formation of higher aliphatic and aromatic hydrocarbons. U.S. Pat. No. 7,148,172 B2 discloses the use of a high silica aluminosilicate chabazite which displays high activity and selectivity for the MTO reaction.

U.S. Pat. No. 4,499,314 discloses methods for converting methanol to hydrocarbons over zeolite catalysts, optionally modified by the addition of compounds of boron, phosphorus, antimony, or silicon into the molecular apertures of the zeolites. U.S. Pat. No. 6,613,951 discloses methods for converting methanol to hydrocarbons over zeolite catalysts, especially ZSM-5 modified by the addition phosphorus oxide. In these methods, aromatic promoter compounds were added to accelerate the reaction.

Attempts were made to minimize formation of heavier hydrocarbons (U.S. Pat. No. 4,387,263) by limiting methanol conversion to 80%. However, under these conditions a large amount of unreacted DME was present which had to be separated from the product stream and recycled.

Due to limitations of ZSM-5 based catalysts for the MTO reaction, attempts were made to develop a second MTO conversion process based on the use of a non-zeolitic molecular sieve catalytic material. Union Carbide Co./UOP developed catalysts comprising a silicoaluminophosphate molecular sieve (SAPO) disclosed in numerous patents such as U.S. Pat. Nos. 5,095,163; 5,126,308; 4,677,242; and 5,191,141. Microporous SAPO catalysts with narrow pore openings (pore diameter ~0.43 nm) are good candidates for the MTO process as their small pore openings allow diffusion of light compounds such as primary alcohols, linear paraffins, and olefins, but not branched isomers and aromatics. By complimenting such morphological characteristics with appropriate levels of acid strength and acid density highly effective MTO catalysts have been designed. Although the catalysts are reported to be superior to previously known MTO catalysts, they degrade rapidly and lose activity in a few hours. Of the SAPO catalysts, SAPO-34 which has the framework of CHA zeolite with 8-ring channels and a pore diameter of 0.38 nm is the most effective for the MTO reaction displaying a selectivity of 80-90% to light olefins (C2-C4) at almost complete conversion of methanol.

The SAPO catalyzed MTO route; however, also generated significant amounts of DME which led to problems of recovery and recycle. U.S. Pat. No. 4,382,263 discloses a method where a relatively high pressure DME absorption zone utilizes a water based solvent in order to capture the DME intermediate. Other attempts relate to using a more efficient DME solvent in the DME absorption zone by diverting a portion of the methanolic feed as disclosed in U.S. Pat. No. 4,587,373. The MTO also process generates a large amount of water which can reduce the catalyst life as well as increase the effluent volumes which lead to increased costs of downstream processing. U.S. Pat. No. 2006/0020155 A1 discloses a method where methanol and/or syngas is converted first to dimethylether (DME) and water over y-alumina catalyst and then converting the resulting DME to a mixture of olefins and water in a second reactor.

Similar to the methanol-to-gasoline reaction, the methanol-to-olefins reaction suffers from a few concerns—

1. highly exothermic reaction leading to a large generation of heat
2. rapid coke build-up due to the small pore size of the catalyst leading to small lifetimes of the catalyst
3. the activity and selectivity of the catalyst cannot be simultaneously increased Various strategies have been proposed to counter these issues such as feed dilution, reducing residence times, and tuning the catalyst acidity. For example, U.S. Pat. No. 6,316,683, discloses a method for protecting the silicoaluminophosphate catalyst by shielding its surface with a template molecule or by a carbonaceous material. U.S. Pat. No. 6,403,854 describes a process which comprises a two-stage quench tower to recover heat and remove impurities for the MTO reaction.

Coupled Reaction System:

One strategy that has been proposed to manage the large exotherm during the methanol-to-hydrocarbon reaction has been to couple this reaction with an endothermic reaction which would make the overall reaction energy neutral. Martin et al. ("Coupled Conversion of Methanol and C4 Hydrocarbons to Lower Olefins, Applied Catalysis, 50 (1989), pp. 149-155") proposed the CMHC (coupled methanol-hydrocarbon cracking) process which consists of integrating the exothermic transformation of methanol to hydrocarbons with an endothermic cracking of naphtha/n-butane over a HZSM-5 catalyst.

Typically, light alkane dehydrogenation to generate olefins is carried out over noble metal-based catalysts (supported Pt—Sn) or metal oxide catalysts (promoted $Cr_2O_3$) though catalyst formulations based on vanadium, molybdenum, gallium and carbon have also been extensively studied. These reactions are reversible, equilibrium-limited and highly endothermic and hence require high temperatures (500-600° C.) and low pressures to obtain desired yields. Apart from the large heat input requirements, these processes suffer from coke formation on catalysts requiring frequent regeneration and irreversible catalyst deactivation due to sintering, volatilization and phase transformations.

Olefins have also been obtained from light alkanes and naphtha by cracking over solid-acid catalysts. The acid sites act as the dehydrogenation function but also facilitate the oligomerization, aromatization, hydrogenation and isomerization of the olefin products resulting in a slew of by-products and consequently equilibrium limitations are overcome. Literature studies (Lu et al. "FeHZSM-5 molecular sieves—Highly active catalysts for catalytic cracking of isobutane to produce ethylene and propylene" Catalysis Communications 7 (2006), 199-203; Hajheidary et al. "Olefins production from LPG via dehydrogenative cracking over three ZSM-5 catalysts" Journal of Scientific & Industrial Research, Vol. 72, December 2013, pp. 760-766) report over 60 wt % light olefin yields from lower alkanes over modified ZSM-5 catalysts. Similar to alkane dehydrogenation over metal catalysts, alkane cracking over acid catalysts is also a highly endothermic reaction and requires large inputs of heat.

A number of studies have addressed the integration of alkane cracking (endothermic reaction) and MTO (exothermic reaction) in the same reactor thus allowing the generation of olefins under energy-neutral conditions. Most of these studies used a silicoaluminate zeolite (HZSM-5 or its modified form) as the catalyst. Lücke et al., in "CMHC: couple methanol hydrocarbon cracking Formation of lower olefins from methanol and hydrocarbons over modified zeolites, Microporous and Mesoporous Materials," (1999) 145-157 disclosed a method for coupled conversion of n-butane/N-hexane/naphtha and methanol to a mixture of hydrocarbons over a ZSM-5 zeolite based catalyst. The molar ratio of methanol/hydrocarbon is carefully maintained to produce light olefins in a thermoneutral way. However, under the proposed conditions (>600° C.) methanol conversion is complete while there is unconverted hydrocarbon. Additionally, due to the high temperatures there was a significant production of methane and other paraffins. The addition of Fe was reported to slow catalyst deactiviation. They reported overall C2-C4 olefin yields of up to 32 wt % when n-butane was co-fed with methanol (molar ratio MeOH/n-C4=3) over metal modified HZSM-5 at 680° C.

In another study, Mier et al reported steady state C2-C4 olefin yields of up to 20 wt % at 550° C. for the same feed over a HZSM-5 catalyst. (Mier et al., "Synergies in the production of olefins by combined cracking of n-butane and methanol on a HZSM-5 zeolite catalyst," Chem. Eng. J. (2010) 760-769.) Apart from thermoneutrality, Mier et al. showed that compared to the individual reactions of n-butane cracking and methanol to olefins, the integrated reaction showed greater selectivity to C2-C4 olefins, reduced formation of methane and COx, and increased catalyst stability by reducing coke formation. It was also reported that for the CMHC reaction, doping HZSM-5 with Ni and Zn increased the yield of aromatic products (Mier et al. "Catalyst discrimination for olefin production by coupled methanol/n-butane cracking" Applied Catalysis A: General 383 (2010) 202-210; Song et al. "Effect of cofeeding n-butane with methanol on aromatization performance and coke formation over a Zn loaded ZSM-5/ZSM-11 zeolite" Applied Catalysis A: General 470 (2014) 15-23) while doping with Fe enhanced olefin yields (Martin el al. "Coupled conversion of methanol and C4-hydrocarbons (CMHC) on iron-containing ZSM-5 type zeolites" *Applied Catalysis* 57(1), (1990)203-214).

US Pat. No. 2014/0357912 discloses a process where different types of hydrocarbon feeds are cracked in a preheated reactor with a riser over a FCC catalyst. The heat is supplied either by cracking methanol or feeding hot gases obtained by burning catalyst coke in oxygen in a regenerator. U.S. Pat. No. 4,627,911 discloses a thermoneutral process where the heat for gas oil cracking is obtained by methanol cracking. However, this process has lower olefin yields due to high residence times in the riser and high temperature for methanol cracking which leads to increased dry gas production. US Pat. No. 2014/0051900 discloses a similar process where naphtha and methanol are concurrently passed over a modified HZSM-5 at temperatures greater than 550° C. Overall C2-C4 olefin yields of 40-50 wt % have been reported.

Despite these results in generating olefins from combined feeds in a thermoneutral way, most of the above mentioned catalytic studies suffer from high temperature requirements, low catalyst stability and low olefin yields. Since most of the above mentioned studies use ZSM-5 and its modified forms as the catalyst, catalyst deactivation due to coke formation and irreversible catalyst deactivation due to dealumination can be expected.

SUMMARY OF INVENTION

The invention provides a method of producing a high-octane gasoline blendstock—alkylate—from a feed comprising of methanol and mixed-butanes. The term "alkylate" refers to the reaction product of isobutane with olefins. High-octane alkylate is the cleanest gasoline blending stream produced in a refinery. Alkylate is an ideal clean fuel component because pollution from alkylate is low and alkylate has low toxicity. In an alkylation reaction, light olefins (typically from a FCC cracker unit) are reacted with iso-paraffins (typically iso-butane) in the presence of a strong acid catalyst.

In a first aspect, the invention provides a method of producing alkylate, comprising: passing methanol and/or dimethylether (DME) into a reaction chamber; and passing butane into the reaction chamber. The reactor comprises a catalyst that is a crystalline zeotype material in which tetrahedral $[TiO_4]$ and $[SiO_4]$ units are arranged in a MFI structure with a three-dimensional system of channels having a molecular dimension of 4.9 to 5.9 Å, preferably 5.1-5.6 Å, and at least 0.5 mass % Ti, more preferably at least 1% Ti, in some embodiments in the range of 1 to 5 mass % Ti. The methanol and/or DME and the butane are reacted in the reaction chamber in the presence of the catalyst to make olefins under steady state conditions where the reaction is adiabatic or nearly adiabatic such that +/−200 kJ/(kg olefin produced) or less is transferred from the reaction chamber (preferably +/−100 or less, more preferably ±50 or less, and still more preferably +/−10 kJ/(kg olefin produced) or less is transferred from the reaction chamber. Then, the olefins with iso-butane are reacted to form alkylate in a separate reactor. The butane could be n-butane or isobutane or mixtures thereof with relatively higher ratios of isobutane being preferred. The reaction enthalpy value is based on steady state operation where heat is either added or removed in order to obtain a steady state temperature (which could be a single temperature or, more typically, a temperature profile) within the reaction chamber.

In another aspect, the invention provides a method of producing olefins, comprising: passing methanol and/or dimethylether (DME) into a reaction chamber; wherein the reactor comprises a catalyst that is a crystalline zeotype material in which tetrahedral [$TiO_4$] and [$SiO_4$] units are arranged in a MFI structure with a three-dimensional system of channels having a molecular dimension of 4.9 to 5.9 A, preferably 5.1-5.6 Å, and at least 0.5 mass % Ti, more preferably at least 1% Ti, in some embodiments in the range of 1 to 5 mass % Ti; and reacting the methanol and/or DME in the reaction chamber in the presence of the catalyst to make olefins. This method may further include a coupled dehydrogenation/cracking reaction of butane(s). If this method is conducted without a coupled reaction, then it will typically include heat exchange such as provided by a heat exchanger adjacent to the reaction chamber.

In a further aspect, the invention provides a method of making C2-C6 olefins from methanol and/or DME, comprising: passing a stream of methanol and/or DME over a catalyst in a reaction chamber. The catalyst comprises a crystalline zeotype material comprising: a system of channels having a pore limiting diameter of 4.9-6.2 Å, at least 0.5 wt % Ti and a Si/Ti ratio of at least 5; and possessing high hydrothermal stability as exhibited by the capability to meet the test conditions of FIG. 5 (that is, if exposed to 1.0 l/hr DME at 475° C. for 8 hours at which time DMV conversion remains at 100% with an olefin selectivity greater than 85%) or possessing high hydrothermal stability such that, if the catalyst is steamed at 600° C. for 3 hours in 1 atmosphere steam, the catalyst exhibits less than 10% loss in surface area as measured using the Brunauer-Emmett-Teller (BET) method. In this method, conditions in the reaction chamber are controlled so that the temperature in the reaction chamber is in the range of 300 to 600° C.; wherein at least 90 wt % of the methanol and/or DME is converted to products in the reaction channel to form a product stream; and collecting the product stream which comprises at least 70 mol % C2-C6 olefins; and wherein the selectivity to C2-C6 olefins decreases by less than 10% over a period of at least 8 hours of continuous operation without regenerating the catalyst. The high hydrothermal stability characteristic mentioned in this inventive aspect is a property of the catalyst which can be measured according to one or both of the mentioned test conditions; it should be understood that these test conditions are not required steps in the process but are specified physical properties of the catalyst.

In a still further aspect, the invention provides a staged reactor system for the synthesis of light olefins, comprising: a reactor comprising plural alternating first and second zones in a series of at least two first zones alternating with at least two second zones; and a flow path through the series of plural alternating first and second zones; wherein the first zones comprise a first catalyst and an inlet for methanol or DME; wherein the first catalyst comprises a crystalline Si/Ti zeotype material of the type described herein for the conversion of DME to olefins; wherein the second zone comprises a dehydrogenation or cracking second catalyst; and wherein the first and second catalysts are different. During operation, the staged reactor system comprises butane in the flow path and DME in the first zones. In preferred embodiments, the dehydrogenation or cracking second catalyst comprises at least 1, or at least 2, or at least 5 wt %, or any of these minimum amounts with an upper bound of 25, or 20, or 15, or 10 wt % of Pt, Pd, Nickel, Cobalt, Copper, Zinc, Iron, Ru, Rh, Sn, or combinations thereof; in some preferred embodiments, the second catalyst comprises Ni or Ni and Zn or Ni and Sn or Ni and Cu.

In any of the inventive aspects, various embodiments of the invention may be further characterized by one or any combination of the following features: the zeotype catalyst may consist essentially of the elements Si, Ti, 0 and, optionally, H; the reaction chamber may contain a second catalyst for dehydrogenation/cracking of butane(s) may further comprise at least 1, or at least 2, or at least 5 wt %, or any of these minimum amounts with an upper bound of 25, or 20, or 15, or 10 wt % of Pt, Pd, Nickel, Cobalt, Copper, Zinc, Iron, Ru, Rh, Sn, or combinations thereof, in some preferred embodiments, Ni or Ni and Zn or Ni and Sn or Ni and Cu; the reaction chamber comprises a temperature in the range 300 and 600° C., preferably 400 and 550° C.; wherein the step of reacting methanol and/or DME is conducted at a pressure between 1 atm and 10 atm (since, for coupled reactions, the reaction chamber can be shared, the temperature and pressure of the dehydrogenation/cracking reaction is the same or substantially similar to those for the conversion of methanol and/or DME); wherein the reactants (methanol and/or DME and butane) flows into the reaction chamber at a GHSV between 100 and 1000 l/hr; wherein the butane comprises a mixture of n-butane and iso-butane; wherein the feed off butane to DME ratio is in the range of 1.0 to 20 mol/mol; wherein the n-butane to iso-butane ratio is 0.1 to 10 mol/mol, or between 1:1 and 2.5:1; or wherein the butane comprises at least 90 mol % isobutane or at least 95 mol % isobutene; where the olefin selectivity is >50 mol %, or >70 mol %, or >80 mol % and, in some embodiments with an upper limit of about 90% (these levels can apply to the conversion of methanol and DME or apply to the coupled reaction including butane(s) to olefin (in this context, the term "olefin" refers to unsaturated compounds comprising from 2 to 6 carbon atoms in the chain; the term "selectivity" is the fraction of the moles of olefins produced as a percent of total moles of products from the reaction, and is measured prior to the (optional) step of reacting olefins with isobutane to produce alkylate, that occurs in a separate reactor); the selectivities are preferably obtained in conjunction with conversion of methanol plus DME of at least 50%, preferably at least 75%, and still more preferably at least 95%; the paraffin selectivity <50 mol %, or <20 mol %, or <15 mol %, and in some embodiments in the range of about 20 to about 9 mol %; where the aromatic selectivity <10 mol %, or <5 mol %, and in some embodiments down to about 2 mol %; where the reaction chamber comprises a fixed-bed catalyst; where the methanol and/or DME feed is staged over a catalyst bed (i.e., staged along the length of a catalyst bed); where the number of methanol and/or DME feed stages is >2; further comprising regenerating the catalyst in flowing air at a temperature of at least 400° C. and a GHSV of at least 500; wherein the catalyst is regenerated in flowing oxygen at a temperature of at least 400° C. and a GHSV of at least 500; wherein the method is run continuously for a period >8 or >12 hours without regenerating the catalyst (the continuous method can be for all steps in the method or may only apply to the catalytic conversion of methanol and/or DME to olefins); wherein the step of reacting the olefins with iso-butane is conducted in the presence of a liquid or solid acid catalyst; wherein the step of reacting the olefins with iso-butane is conducted in the presence of a solid acid catalyst selected from the group consisting of zeolites, silica-aluminas, tung stated zirconia and sulfated zirconia; wherein the step of reacting the olefins with iso-butane is conducted in the presence of a liquid acid catalyst selected from the group of HF, sulfuric acid, AlCl3, ionic-liquids and triflic acid; further comprising a step of passing at least a portion of the olefins through a methyl-tert-butyl ether (MTBE) unit to produce an MTBE raffinate and then alkylating the MTBE raffinate; wherein the alkylate comprises 5 or 3 or 1 mass % aromatics or less; and/or wherein the alkylate has a MON of at least 88, or a MON of about 90.

The invention may include a method of alkylating isobutane, comprising, under steady state conditions, passing a feed mixture of isobutane and C2-05 olefins (which is typically conducted in a continuous fashion) into a reaction chamber such that the weight of olefin fed per weight of catalyst before regeneration (catalyst age) is 2.5 or greater and producing 5 kg of alkylate product per kg of catalyst or greater wherein the olefin conversion remains above 90%, and the Research Octane Number (RON) of the products remains above 92. Steady state means that the selectivity to C8 isomers changes by 10% or less over a time period in which the 5 kg of alkylate product is produced per kg of catalyst. For example, a change in selectivity from 80% to 72% would be a 10% change. In this method, the reaction chamber comprises a crystalline zeolite catalyst; wherein the crystalline zeolite catalyst comprises sodalite cages and supercages, a Si/Al molar ratio of 20 or less, less than 0.5 weight percent alkali metals, and rare earth elements in the range of 10 to 35 wt %. Optionally, the catalyst may comprise up to 5 wt % Pt and/or Pd; and/or Nickel.

Glossary

As is conventional, "aromatic" refers to any compound containing an aromatic ring.

Conversion—The term "conversion of a reactant" refers to the reactant mole or mass change between a material flowing into a reactor and a material flowing out of the reactor divided by the moles or mass of reactant in the material flowing into the reactor. For example, if 100 grams of olefin are fed to a reactor and 10 grams of olefin exit the reactor, the conversion is [(100−10)/100]=90% conversion of olefin.

A "crystalline zeotype material" means the material can be detected by x-ray diffraction and that it possesses a three dimensional silica framework with open channels into the material. The materials are also called zeolite structures. A description of a large number of zeolite structures can be found in the Zeomics structural compendium through the website http://helios.princeton.edu/zeomics/; although measurements of channel openings in specific catalysts should be determined by conventional techniques. Although typical zeolites are aluminosilicates, aluminum is not necessary in the catalysts used in the present invention that preferably contain less than 1 wt % Al, preferably <0.5 or <0.1 or <0.01 wt % Al; unless otherwise specified, these compositions refer to the catalyst including binder or, in some preferred embodiments refer to the composition within the crystalline phase. The crystalline zeotype catalyst used for converting methane and/or DME to olefins can be referred to as Si/Ti zeotype catalyst indicating Ti in the zeolite Si—O framework.

"MON" stands for motor octane number and is a well-known measure of fuel quality.

Olefins—As used herein, the term "olefin" has its ordinary meaning in the art, and is used to refer to any unsaturated hydrocarbon containing one or more pairs of carbon atoms linked by a double bond. The term light olefins refers to C2-C6 olefins. In this invention, C2-C6 olefins refers to ethylene, propylene, n-butylenes, isobutylene, and the various isomers of pentene and hexene. The phrase "C2-C6 olefins" has the standard meaning encompassing any combination of olefins in the C2 to C6 range, with no minimum requirement for any of the C2 to C6 compounds.

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et at, "Fundamentals of Powder Diffraction and Structural Characterization of Materials," Springer Science+Business Media, Inc., New York, 2005. Other techniques that may be useful in determining pore sizes (e.g., zeolite pore sizes) include, for example, helium pycnometry or low-pressure argon adsorption techniques. These and other techniques are described in Magee, J. S. et at, "Fluid Catalytic Cracking: Science and Technology," Elsevier Publishing Company, Jul. 1, 1993, pp. 185-195. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, As is conventional, the phrase "having a molecular dimension of 5.1-5.6 Å" (or the like) refers to the largest channel openings within the MFI structure (not the largest cavity sizes) which limit the size of compounds that can escape the interior of the zeolite. This may also be known as the pore limiting diameter. The presence of the MFI structure can be characterized by x-ray diffraction (XRD), $N_2$ adsorption-desorption isotherms. An example is presented by Silvestre-Albero et al., "Desilication of TS-1 zeolite for the oxidation of bulky molecules," Cat. Comm. 44 (2014) 35-39. As is conventionally understood, the phrase "tetrahedral titania" does not require the titania to be exactly tetrahedral, but that it meets the characteristic values for Ti-substituted zeolites such as those mentioned in conjunction with the paper by Silvestre-Albero et al. As is conventionally known, the stated molecular dimensions within the crystalline structure can be determined by known techniques, particularly the conventional gas adsorption/desorption technique such as that described in the paper by Silvestre-Albero et al. The techniques for determining pore structure should converge to the same values; however, if there is a significant discrepancy, the gas adsorption/desorption technique described in the paper by Silvestre-Albero et al. will be determinative.

Selectivity—The term "selectivity" refers to the amount of production of a particular product (or products) as a percent of all products resulting from a reaction. For example, if 100 grams of products are produced in a reaction and 80 grams of octane are found in these products, the selectivity to octane amongst all products is 80/100=80%. Selectivity can be calculated on a mass basis, as in the aforementioned example, or it can be calculated on a molar basis, where the selectivity is calculated by dividing the moles a particular product by the moles of all products. Unless specified otherwise, selectivity is on a mass basis.

Yield—The term "yield" is used herein to refer to the amount of a product flowing out of a reactor divided by the amount of reactant flowing into the reactor, usually expressed as a percentage or fraction. Mass yield is the mass of a particular product divided by the weight of feed used to prepare that product.

When unspecified, "%" refers to mass % which is synonymous with weight %. Ideal gas behavior is assumed so that mole % is the same as volume % in the gas phase.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components. As is standard terminology, "systems" include to apparatus and materials (such as reactants and products) and conditions within the apparatus.

DETAILED DESCRIPTION OF THE INVENTION

Methanol and butanes can be converted to alkylate using a 3-step process as illustrated below:

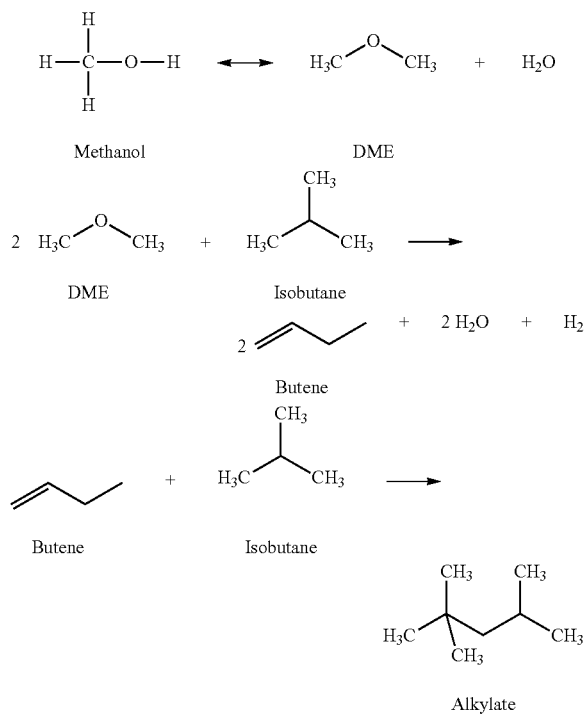

Step 1. Conversion of Methanol to Dimethyl Ether. Methanol can be partially dehydrated to an equilibrium mixture of dimethyl ether (DME), methanol and water over a solid-acid catalyst (typically γ-alumina). This reaction is rapid, reversible and exothermic. Water can be removed to drive the reaction. In cases where the starting material is DME rather than methanol, the first step can be omitted. Although DME is the preferred reactant for Step 2, methanol or a mixture of methanol and DME can be used in place of the DME in Step 2.

Step 2: Simultaneous conversion of DME and butanes to light olefins over a fixed-bed catalyst: DME and butanes are reacted in a coupled reaction to form light olefins such as ethylene, propylene, butylene and mixtures thereof. The conversion of DME to olefins is an exothermic reaction ($\Delta H=-55$ kJ/mole) while the dehydrogenation of butanes to olefins is an endothermic reaction ($\Delta H=120$ kJ/mole). Coupling the two reactions simultaneously, by reacting about 2 moles of DME per mole of isobutane results in a thermo-neutral reaction, which allows one to design a simple, fixed-bed process.

Step 3: Alkylation of iso-butane with light olefins: Water, BTX and hydrogen are first removed from the effluent from the second stage and then the remaining light olefins are mixed with excess iso-butane and reacted over a solid-acid catalyst to produce high-octane alkylate. The alkylation catalyst comprises a crystalline zeolite structure with a Si/Al molar ratio of 20 or less and up to 5 wt % of Pt, Pd and or Nickel. The reaction can be run liquid phase over a fixed-bed of catalyst at temperatures 35-90° C.

Figure 1:
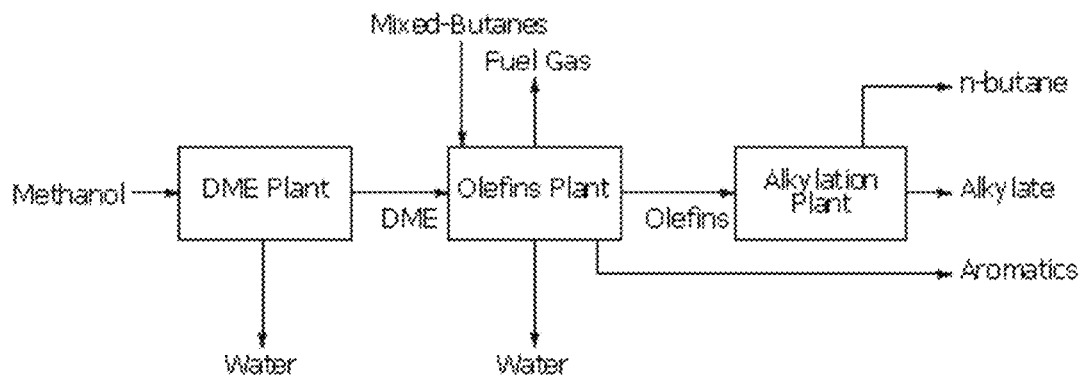
FIG. 1 Three step process for the conversion of methanol and butanes to alkylate.

One possible schematic for the 3 step process is illustrated in FIG. 1. The formation of DME is a conventional process and need not be described here. The alkylation step can be a conventionally known process but is preferably an improved process developed by Exelus Inc. that is described in an earlier patent.

The reactant starting compositions for the inventive processes are methanol and/or DME and butane. The butane can be n-butane, isobutane, or typically a mixture of butanes.

The simultaneous conversion of DME and butanes to light olefins (Step 2) has special challenges. The reactivity of butanes is much lower compared to DME. To compensate for the lower reactivity of butanes, researchers typically use high reaction temperatures (>600° C.) and strong solid acid catalysts to achieve adequate productivity. These solid acid catalysts, however, lead to poor selectivity for the conversion of DME to olefins.

An important feature in the conversion of methanol/DME is the presence of the crystalline zeotype catalyst. The catalyst typically includes binders that do not significantly degrade the catalytic activity of the zeotype catalyst. The catalyst preferably contains at least 20 mass % of the crystalline zeotype catalyst; in some embodiments at least 50 mass % or at least 75 mass % of the crystalline zeotype catalyst. With respect to the catalyst, unless specified otherwise, mass % refers to the mass as a percent of the entire mass of the catalyst including both crystalline and noncrystalline material in the catalyst. A binder need not be present; however, in cases where binder is present, the stated mass % includes binder, unless specified otherwise such as the following: In some embodiments, the Ti content of the crystalline phase comprises at least 0.5 wt % Ti, or at least 1.0 wt % Ti, or from 0.5 to 3.0 wt %.

We have discovered that titanium silicalite-1 (TS-1) is an excellent catalyst for the conversion of DME to light olefins and the simultaneous conversion of DME and butanes to light olefins. Titanium silicalite was developed in 1983 by research workers of Enichem. The synthesis of this catalyst is described, for example, in U.S. Pat. No. 4,410,501 (incorporated herein by reference) and Bruno Notari, "Microporous Crystalline Titanium Silicates", Advances in Catalysis, vol. 41 (1996), pp. 253-334. The SiO2:TiO2 molar ratio of titanium-silicalite molecular sieve can range from 10 to 200. This zeolite shows several interesting properties in heterogeneous oxidation catalysis. TS-1 shows good activity and selectivity in alcohol oxidation, alkane oxidation, alkene epoxidation and ammoximation of cyclohexanone to cyclohexanone oxime.

Figure 2:
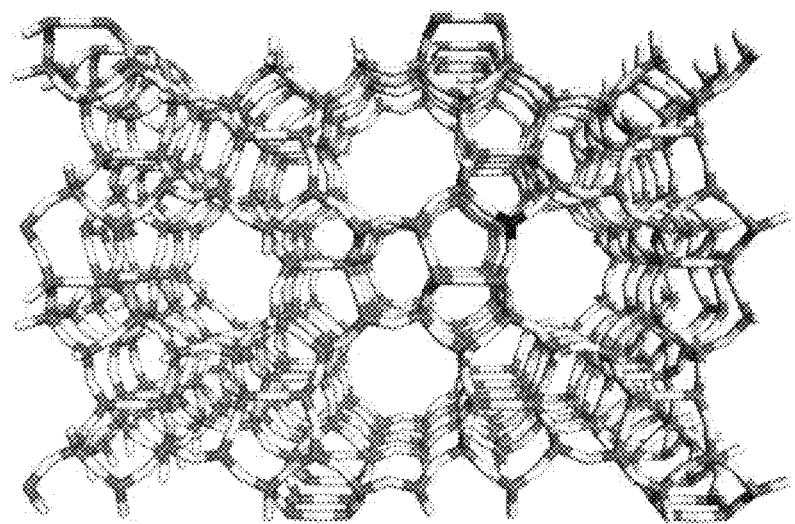
FIG. 2. Structure of Titanium-Silicalite molecular sieve
FIG. 3. Distributed feed fixed-bed reactor design for the conversion of DME and butanes to light olefins.

TS-1 is a highly structured zeolite type material comprising of titania and silica arranged in a MFI structure similar to ZSM-5 without the strong acidity. The structure is shown in FIG. 2. It has a 3-D micro-porous zeolitic structure with a medium pore size (i.e., channel opening size of about 5.5 A) which provides the right shape-selectivity towards lower molecular weight products. Generally, the titanium species in TS-1 can be categorized into two types: framework Ti atoms substituted into the silica lattices and extra framework Ti atoms. Ideally, the Ti atoms are supposed to be incorporated into the lattice as isolated entities and should be surrounded by four $OSiO_3$ tetrahedra. Studies have shown that the overall acidity as well as the number of Brönsted acid sites increase with the increase in Ti content of TS-1. We have found that TS-1 based catalysts are excellent candidates for the simultaneous conversion of DME/butanes to light olefins for reasons listed below.

1. Moderate Acid Support: The high acid strength of zeolites like ZSM-5 and H-Beta favors reactions like the aromatization and hydrogenation of olefins suggesting that moderate or weak acid strength are preferred for the methanol or DME to olefins reaction. TS-1 which is a weak acid zeolite is thus a desirable support for converting methanol and its derivatives to light olefins.

2. Optimal Pore structure: TS-1 is a highly structured zeolite type material consisted of titania and silica arranged in a MFI structure similar to ZSM-5 without the strong acidity. It has a 3-D micro-porous zeolitic structure with a medium pore size (about 5.5 A) which provides the right shape-selectivity towards lower molecular weight products (e.g. light olefins) as opposed to amorphous catalysts like silica, silica alumina and zirconia.

3. High Hydrothermal Stability: The methanol or DME to olefins reaction generates significant amounts of water which results in gradual catalyst deactivation depending on the support used. TS-1 is routinely used as a catalyst for the formation of epoxides from olefins using organic peroxides which generates significant amounts of water and still displays excellent hydrothermal stability over a large period of time.

These characteristics provide guidance for selecting appropriate catalysts for the inventive process. The use of Ti-substituted zeolite provides the desired acid strength. Preferred ratios of Si/Ti are 15 to 150, or 20 to 100, or 25 to 50. The limiting pore size is controlled to accommodate the critical sizes of methanol (4.4 Å), ethylene (4.2 Å), propylene (5.0 Å), and butene (5.1 Å) while excluding aromatics (6.7 Å or greater). The requisite hydrothermal stability can be easily measured and excludes the common aluminosilicates which are unsuitable for the inventive process.

The same catalyst can be used for both of the coupled reactions—DME to olefins and butanes to olefins; however, due to its cost and low acid strength, TS-1 is not an ideal catalyst for the conversion of butanes to olefins. To improve its activity for dehydrogenation of butane, metals can be added to the TS-1 catalyst. Alternatively, catalysts having different acid strengths can be disposed in separate zones within a reaction chamber to conduct the coupled reaction. The DME to olefins catalyst preferably consists of at least 95% Si, Ti, and O; more preferably at least 97%; and in some embodiments at least 99% Si, Ti, 0, and, optionally, H. The butane to olefins catalyst, on the other hand, may contain a variety of metals. For example, in some preferred embodiments, the second catalyst comprises at least 1, or at least 2, or at least 5 wt %, or any of these minimum amounts with an upper bound of 25, or 20, or 15, or 10 wt % of Pt, Pd, Nickel, Cobalt, Copper, Zinc, Iron, Ru, Rh, Sn, or combinations thereof; these metals are disposed on a catalyst support; and in some preferred embodiments, the catalyst support is selected from the group consisting of carbon, $SiO_2$, $Al_2O_3$, $TiO_2$, $ZrO_2$, $CeO_2$, $Y_2O_3$, Silica-Alumina, Zeolite Y, Zeolite USY, Zeolite ZSM-5, TS-1, Zeolite Beta, Zeolite Mordenite or combinations thereof.

The reaction chamber can contain a fixed bed reactor or other reactor type. The methanol or DME can be reacted over the Ti-substituted zeolite in the same reactor volume in which the butane(s) is reacted; more preferably, the reactions are conducted in separate zones—with the methanol/DME reaction zone containing the Ti-substituted catalyst (preferably without added metal) and the dehydrogenation and cracking of butane(s) conducted over a metal-containing catalyst in a second reaction zone. The zones can be alternated within a reactor with heat from the exothermic reaction of methanol/DME carried into the zone where the dehydrogenation and cracking of butane(s) is conducted. The reactor can be insulated (for adiabatic or near adiabatic operation) or operated in conjunction with a thermally-connected heat exchanger (typically adjacent or surrounding the reactor) for adding or removing heat to/from the reactor.

This invention provides methods of converting isobutane and DME to light olefins comprising: passing a feed of isobutane and DME into a reaction chamber comprising alternating beds of a crystalline zeolite catalyst with MFI structure comprised of silicon and titanium oxides and up to 15 wt % of Pt, Pd, Nickel, Cobalt, Copper, Zinc, Iron, Ru, Rh, Sn or combinations thereof and a crystalline zeolite catalyst with MFI structure comprised of silicon and titanium oxides such that the DME feed is staged over the crystalline zeolite catalyst with MFI structure comprised of silicon and titanium oxides (substantially without added elements other than Ti) while mixed butanes flow in a plug flow manner over both groups of catalyst. The dehydrogenation/cracking catalyst need not have the MFI structure and could be any suitable dehydrogenation/cracking catalyst. In this case, it is desirable for the reaction to be carried out under conditions such that the DME is at least 90% consumed, preferably at least 95% consumed in the DME-conversion zone and prior to contacting the dehydrogenation/cracking catalyst.

Figure 3:
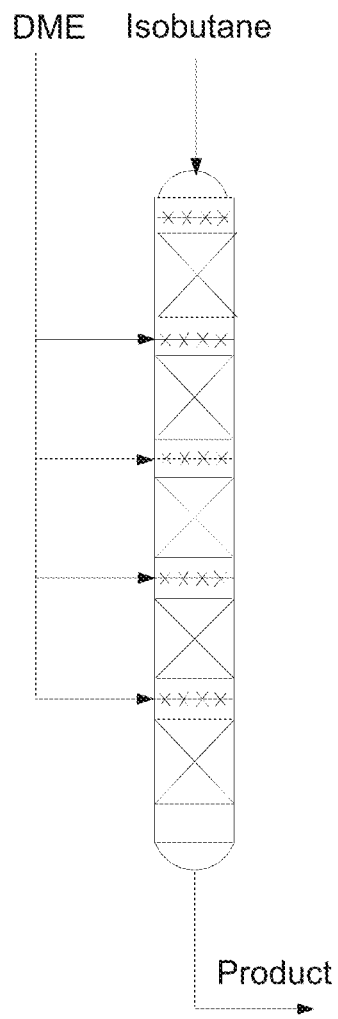

The invention also relates to a reactor system suitable for paraffin alkylation using solid acid catalysts. Fixed-bed reactors are easier to design, scale-up and maintain and, therefore, preferred embodiments utilize a fixed bed reactor. In some preferred embodiments of the invention, the DME feed is staged over multiple beds to control temperature profile. FIG. 3 schematically illustrates a distributed feed fixed-bed reactor design for the conversion of DME and butanes to light olefins.

In this type of staged reaction, the initial drop in temperature due to butane dehydrogenation or cracking reaction is compensated by a corresponding rise in temperature by the DME to olefins reaction. The extent of butane dehydrogenation or cracking and DME conversion to olefins is controlled largely the respective residence times over the catalyst beds. A secondary benefit of this arrangement is the significant boost in olefin selectivity caused by the dilution effect from butane flow. A reduction in the partial pressure of the olefin leads to a large decrease in the amount of aromatics or paraffin production which allows a high selectivity to light olefins. Another benefit of this arrangement is the ability to tailor the catalyst to the specific reaction.

Butane dehydrogenation or cracking is a slower reaction than the production of olefins from DME. The ability to stage alternating types of catalyst allows one to design one set of catalyst primarily for butane dehydrogenation/cracking reaction and another set of catalyst for the DME to olefins reaction. The typical fluidized bed reactors used for the MTG, MTO or CMHC process do not allow for such an approach.

In some embodiments, the inventive methods may be further characterized by specified parameters. The conversion of DME and butanes to olefins is preferably conducted at a pressure between 1 atm and 10 atm. The reactants (methanol and/or DME and butane) preferably flow into the reaction chamber at a GHSV of at least 50 or at least 100 or between 100 and 1000 l/hr. In the broadest sense, the term "butane" should be understood as either n-butane or isobutane, or a mixture of butane types. In some embodiments, the method is conducted with a butane feed having an n-butane to iso-butane ratio of 0.1 to 10 mol/mol, or between 1:1 and 2.5:1; or wherein the butane comprises at least 90 mol % isobutane or at least 95 mol % isobutane. The ratio of butane/DME in the feed stream can be controlled to balance the enthalpies of reaction; preferably, the feed butane to DME ratio is in the range of 1.0 to 20 mol/mol. In operation, the catalyst(s) can be regenerated in flowing air or oxygen at a temperature of at least 400° C. and a GHSV of at least 500.

For either the DME to olefin reaction or for the combined, coupled reactions, the olefin selectivity is >50 mol %, or >70 mol %, or >80 mol % and, in some embodiments with an upper limit of about 90%; the paraffin selectivity is <50 mol %, or <20 mol %, or <15 mol %, and in some embodiments in the range of about 20 to about 9%.

The inventive methods (either DME to olefins or the coupled reaction with DME and butane) can run continuously and at steady state for a period of at least 8 hours or at least 12 hours without regenerating the catalyst. Over this period of steady state operation (without regenerating the catalyst). In preferred embodiments, the conversion of methanol and/or DME and the selectivity to C2-C6 olefins remains constant or changes 10% or less, or 5% or less, for the entire period without regeneration. In some preferred embodiments, the catalyst operates for at least 4 hours without regeneration or at least 8 hours without regeneration or at least 12 hours without regeneration and the conversion of methanol and/or DME and the selectivity to C2-C6 olefins remains constant or changes 10% or less or 5% or less for at least 10 days or at least 20 consecutive days of operation. The consecutive operation typically includes intervening regeneration steps; for example, operating continuously for at least 8 hours, followed by regenerating (typically by oxidizing with air), for example by oxidizing for 0.5 to 6 hours; and then again conducting the conversion to olefins.

The step of reacting the olefins with iso-butane to form alkylate in a separate reactor (Step 3) can be conducted under known conditions. In preferred embodiments the alkylation reaction is conducted over a La-exchanged sodalite-containing catalyst as described in U.S. Published patent application Ser. No. 15/190,063 incorporated herein by reference as if reproduced in full below.

Mukherjee et al. in U.S. Published patent application Ser. No. 15/190,063 describe a method of alkylating isobutane, comprising: under steady state conditions, passing a feed mixture of isobutane and C2-05 olefins (which is typically conducted in a continuous fashion) into a reaction chamber such that catalyst age is 2.5 or greater and producing 5 kg of alkylate product per kg of catalyst or greater wherein the olefin conversion remains above 90%, and the Research Octane Number (RON) of the products remains above 92. Steady state means that the selectivity to C8 isomers changes by 10% or less over a time period in which the 5 kg of alkylate product is produced per kg of catalyst. For example, a change in selectivity from 80% to 72% would be a 10% change. In this method, the reaction chamber comprises a crystalline zeolite catalyst; wherein the crystalline zeolite catalyst comprises sodalite cages and supercages, a Si/Al molar ratio of 20 or less, less than 0.5 weight percent alkali metals, and rare earth elements in the range of 10 to 35 wt %. Optionally, the catalyst may comprise up to 5 wt % Pt and/or Pd; and/or Nickel.

The alkylation catalyst can be made by contacting the zeolite with a solution comprising a rare earth metal; calcining said catalyst by heating said catalyst to a calcination temperature of at least 575° C. to produce a catalyst intermediate comprising the rare earth metal and second concentration of alkali metal that is less than the first concentration of alkali metal; contacting the catalyst intermediate with an ammonium solution, drying to remove excess solution, and then heating the catalyst to generate the hydrogen (active) form of the zeolite—the deammoniation step. It is believed that the deammoniation step converts the ammonium cation sites to Bronsted acid sites, especially in the supercages, while the rare earth elements remain in the sodalite cages. Because the acid, or H+, sites are located in the larger diameter supercage structure of the catalyst, pore mouth plugging is significantly reduced, allowing the catalyst to remain active for increased periods of time, while the rare earth metal cation sites, such as, for example, $La^{+3}$ sites, provide enhanced stability to the sodalite structure.

The invention is further elucidated in the examples below. In some preferred embodiments, the invention may be further characterized by any selected descriptions from the examples, for example, within ±20% (or within ±10%) of any of the values in any of the examples, tables or figures; however, the scope of the present invention, in its broader aspects, is not intended to be limited by these examples.

EXAMPLES

Figure 4:
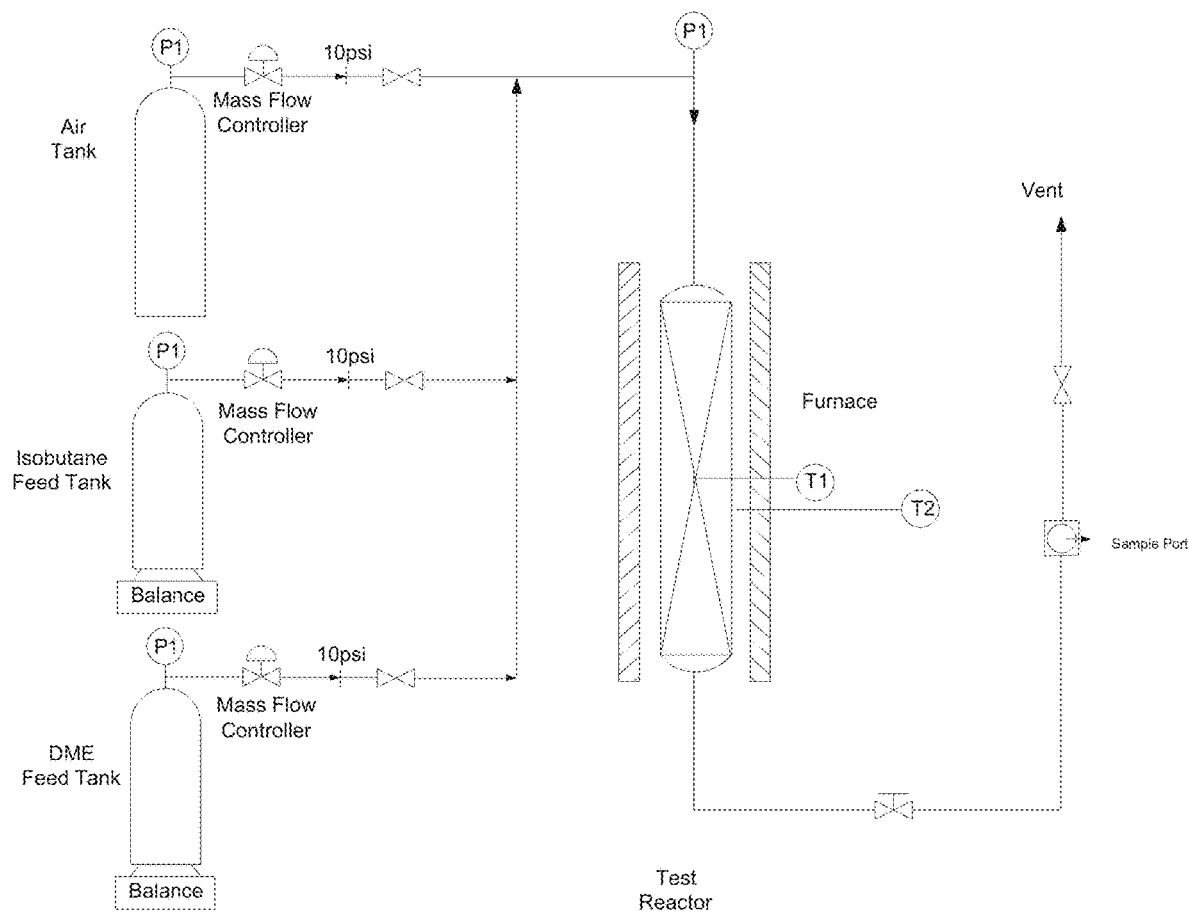
FIG. 4. Catalyst test unit for the conversion of DME and butanes to light olefins.

Catalyst screening experiments were performed using an isothermal packed bed reactor setup as shown in FIG. 4. Heating is controlled using an Omega temperature control unit and a ceramic heating element. Feeds are sent through a preheater of ~75 cm length prior to entering the reactor. The catalyst of interest (1-10 gms) is first loaded into a reactor shown in FIG. 4, a center thermocouple (K-type) is inserted and positioned such that the tip of the thermocouple (3.1 mm diameter) is at the bottom of the catalyst bed. 1 mm glass beads are used to fill any void space in the reactor. The catalyst is activated in dry air at atmospheric pressure at 475° C. (4 hours). Following activation the reactor is then purged with dry nitrogen for 0.5 hours and flow of DME and/or butanes initiated.

Feed and products are analyzed using a HP5890 GC equipped with a Petrocol DH column.

Example 1—Catalyst A

The starting material was a commercial zeolite TS-1, obtained from ACS Materials, (Medford, Mass.) having a Si/Ti molar ratio of ~30 and a surface area of 360-420 m²/g. 5 grams of the zeolite was crushed and sieved to 0.5-1.4 mm particles.

Example 2—Catalyst B

The catalyst is the same commercial TS-1 as Example 1, which was then impregnated with Ni and Zn. The catalyst was simultaneously impregnated with a solution of Ni $(NO_3)_2 \cdot 6H_2O$ and $Zn(NO_3)_2 \cdot 6H_2O$. The salt solution was added, using incipient wetness impregnation, in amounts such that 15 weight percent Nickel was added to the catalyst and the Ni/Zn atomic ratio was 0.57.

The catalyst was then calcined in an oven. The temperature program was: 120° C. (1 hour), 230° C. (2 hours), and 500° C. (4 hours). 5 g of the catalyst was pelletized, crushed and sieved to 1.18-1.4 mm particles

Example 3—Catalyst C

The catalyst was prepared from a high surface area $Al_2O_3$ catalyst, obtained from Alfa Aesar. The catalyst was impregnated with a salt solution of Nickel nitrate and Zinc nitrate and calcined in the same way as Example 2. The catalyst was crushed and sieved into 1.18-1.4 mm particles.

Example 4—Catalyst D

The catalyst was zeolite H-Beta with a Silica-Alumina Ratio (SAR) of 25 and was obtained from Zeolyst. Catalyst was in ammonium form with a surface area of 680 $m^2/g$.

Example 5—Catalyst E

The catalyst was zeolite H-ZSM-5 with a Silica-Alumina Ratio (SAR) of 30 and was obtained from Zeolyst. Catalyst was in ammonium form with a surface area of 425 $m^2/g$.

Example 6—Catalyst F

The catalyst was zeolite H-ZSM-5 with a Silica-Alumina Ratio (SAR) of 280 and was obtained from Zeolyst. Catalyst was in ammonium form with a surface area of 400 $m^2/g$.

Example 7—Catalyst G

The catalyst was high surface area silica with a pore diameter of 150 Å and a surface area of 300 $m^2/g$ and was obtained from Sigma-Aldrich.

Example 8—Catalyst H

The catalyst was high surface area γ-Alumina in ⅛ inch pellet form and was obtained from Alfa Aesar.

Example 9—Catalyst I

The catalyst was Na-Mordenite (obtained from Zeolyst) having a SAR of 13 and surface area of 425 $m^2/g$. The catalyst was converted to the $H^+$ form by first exchanging it with an aqueous solution of 0.5 M Ammonium Nitrate three times for 2 hours each at 80 C. The catalyst was then dried and calcined at 400 C in air.

Example 10—Catalyst J

The catalyst was Amorphous Silica Alumina having a SAR of 14 and was obtained from Sigma-Aldrich. The particle size was 149 micrometer (100 Mesh).

Example 4—Catalyst K

The starting material was a commercial zeolite X having a SiO2/Al2O3 molar ratio of 2.8 (Si/Al of 1.4) and a sodium content of 15% by weight. 5 grams of the zeolite was crushed and sieved to 0.5-1.4 mm particles. They were suspended in 50 mL of deionized water and stirred for 15 minutes after which the water was decanted. This washing procedure was repeated a second time.

A lanthanum ion exchange was performed immediately following the initial water wash. The zeolite was suspended in 50 mL of a 0.2 M lanthanum nitrate solution and heated to 80° C. while stirring for 2 hours. The lanthanum solution was decanted and replaced with a fresh solution. This lanthanum exchange was performed three times followed by 2 water washes of 75 mL each. The zeolite was then left to dry at room temperature.

Following the lanthanum exchange, the zeolite was calcined in a burnout oven. The temperature program for calcination was 1.5° C./min ramp to 100° C. where it was held for 1 hour, 2.0° C./min ramp to 230° C. and hold for 2 hours, 10° C./min ramp to the final calcination temperature of 400° C. for 4 hours.

The lanthanum exchanged zeolite was suspended in a 0.5 M ammonium nitrate solution and heated to 80° C. with stirring for 2 hours. The ammonium solution was decanted and replaced with fresh solution. This ion exchange was performed 3 times followed by 2 water washes of 75 mL each. The zeolite was then left to dry at room temperature. The zeolite was deaminated in dry air (<2 ppm) using the following temperature program: 100° C. (0.5 hours), 120° C. (1 hour), 230° C. (2 hours), 400° C. (4 hours). 400° C. is the deamination temperature required to convert the catalyst from the ammonium form to the active proton form. The lower temperatures are necessary to completely dry the catalyst.

1. Catalyst A (titanium silicalite TS1 from ACS Material, Medford, Mass.) was used. Experiments were performed using an isothermal packed bed reactor setup described above. The catalyst (5 gm) is first loaded into a reactor shown in FIG. 3, a center thermocouple (K-type) is inserted and positioned such that the tip of the thermocouple (3.1 mm diameter) is at the bottom of the catalyst bed. 1 mm glass beads are used to fill any void space in the reactor. The catalyst is activated in dry air at atmospheric pressure at 475° C. (4 hours). Following activation the reactor is then purged with dry nitrogen for 0.5 hours. Iso-butane was fed at 5 gm/hr using a mass flow controller. The reaction was then conducted at 475° C., WHSV=1.0 l/hr and atmospheric pressure. The products were analyzed using a HP5890 GC equipped with a Petrocol DH column The isobutane conversion was less than 1%.

2. Catalyst B (Ni/Zn/TS-1) was used. Experiments were performed using an isothermal packed bed reactor setup described above. The catalyst of interest (5 g) is first loaded into a reactor and activated in dry air. Iso-butane was fed at 5 gm/hr using a mass flow controller.

The isobutane conversion was 25% and olefin selectivity >80%.

3. Catalyst B (Ni/Zn/Alumina) was used. Experiments were performed using an isothermal packed bed reactor setup described above. The catalyst of interest (5 g) is first loaded into a reactor and activated in dry air. Iso-butane was fed at 5 gm/hr using a mass flow controller.

The isobutane conversion was 7% and olefin selectivity >90%.

TABLE 1

Performance of catalysts for iso-butane conversion to light olefins

| Catalyst | Description | iso-Butane Conversion (%) | Product Selectivity (%) | | | |
|---|---|---|---|---|---|---|
| | | | Olefin | Paraffin | BTX | COx |
| A | TS-1 | 0.4 | 22 | 75 | 3 | 0 |
| B | Ni-Zn/TS-1 | 25 | 82 | 15 | 3 | 0 |
| C | Ni-Zn/γ-Alumina | 7 | 90 | 9 | 1 | 0 |

The results clearly show that a bi-functional catalyst with both metal and adequate acid functions are required to convert iso-butane to light olefins.

4—Catalyst A titanium silicalite TS1 from ACS Material, Medford, Mass.) was used. Experiments were performed using an isothermal packed bed reactor setup. Heating is controlled using an Omega temperature control unit and a ceramic heating element. The catalyst (5 gm) is first loaded into a reactor shown in FIG. 3, a center thermocouple (K-type) is inserted and positioned such that the tip of the thermocouple (3.1 mm diameter) is at the bottom of the catalyst bed. 1 mm glass beads are used to fill any void space in the reactor. The catalyst is activated in dry air at atmospheric pressure at 475° C. (4 hours). Following activation the reactor is then purged with dry nitrogen for 0.5 hours. DME with nitrogen as diluent was fed at 5 gm/hr using a mass flow controller. The reaction was then conducted at 475 C, WHSV=1.0 l/hr and atmospheric pressure. The products were analyzed using a HP5890 GC equipped with a Petrocol DH column.

The test results are shown in table 2. The DME conversion remained constant at 100% for 24 hrs while the olefin selectivity >85 wt %.

5. Catalyst D zeolite H-Beta with a Silica-Alumina Ratio (SAR) of 25 was used. The catalyst was tested as in example 4. The test results are shown in table 2. The DME conversion was 78% while the olefin selectivity was 12 wt %.

6. Catalyst E The catalyst was zeolite H-ZSM-5 with a Silica-Alumina Ratio (SAR) of 30 and was obtained from Zeolyst. Catalyst was in ammonium form with a surface area of 425 m$^2$/g. The catalyst was tested as in example 4. The test results are shown in table 2. The DME conversion was 100% while the olefin selectivity was 52 wt %.

7. Catalyst F The catalyst was zeolite H-ZSM-5 with a Silica-Alumina Ratio (SAR) of 280 and was obtained from Zeolyst. Catalyst was in ammonium form with a surface area of 400 m$^2$/g. The catalyst was tested as in example 4. The test results are shown in table 2. The DME conversion was 100% while the olefin selectivity was 28 wt %.

8. Catalyst G The catalyst was high surface area γ-Alumina in ⅛ inch pellet form and was obtained from Alfa Aesar. The catalyst was tested as in example 4. The test results are shown in table 2. The DME conversion was 100% while the olefin selectivity was 0 wt %.

9. Catalyst G The catalyst was high surface area silica with a pore diameter of 150 Å and a surface area of 300 m$^2$/g and was obtained from Sigma-Aldrich. The catalyst was tested as in example 4. The test results are shown in table 2. The DME conversion was 28% while the olefin selectivity was 12 wt %.

10. Catalyst I The catalyst was Amorphous Silica Alumina having a SAR of 14 and was obtained from Sigma-Aldrich. The particle size was 149 micrometer (100 Mesh). The catalyst was tested as in example 4. The test results are shown in table 2. The DME conversion was 100% while the olefin selectivity was 19 wt %.

11. Catalyst I The catalyst was Na-Mordenite (obtained from Zeolyst) having a SAR of 13 and surface area of 425 m$^2$/g. The catalyst was converted to the 1-1±form by first exchanging it with an aqueous solution of 0.5 M Ammonium Nitrate three times for 2 hours each at 80° C. The catalyst was then dried and calcined at 400° C. in air. The catalyst was tested as in example 4. The test results are shown in table 2. The DME conversion was 87% while the olefin selectivity was 45 wt %.

TABLE 2

Performance of catalysts for DME conversion to light olefins ($C_2$—$C_6$)

| Catalyst | Description | DME Conversion (%) | Product Selectivity (%) | | | |
|---|---|---|---|---|---|---|
| | | | Olefin | Paraffin | BTX | COx |
| A | TS-1 | 100 | 89 | 9 | 2 | 0 |
| D | H-Beta(25) | 78 | 12 | 75 | 13 | 0 |
| E | ZSM-5 (30) | 100 | 52 | 27 | 21 | 0 |
| F | ZSM-5 (280) | 100 | 28 | 61 | 11 | 0 |
| G | γ-Alumina | 100 | 0 | 66 | 0 | 34 |
| H | Silica | 28 | 5 | 76 | 0 | 19 |
| I | Silica-Alumina (14) | 100 | 19 | 77 | 1 | 3 |
| J | Mordenite (13) | 87 | 45 | 52 | 3 | 0 |

As shown clearly above, Catalyst A (TS-1) is the best performing catalyst for the production of light olefins from DME.

TABLE 3

Detailed product distribution for production of hydrocarbons from DME using catalyst A (TS-1)

| Hydrocarbon | Olefin | Paraffin | BTX |
|---|---|---|---|
| Methane | | 2.0% | |
| Ethylene | 4.0% | 0.1% | |
| Ethane | | 0.0% | |
| Propylene | 40.0% | | |
| Propane | | 0.4% | |
| Butanes | | 1.0% | |
| Butenes | 28.5% | | |
| Pentanes | | 1.0% | |
| Pentenes | 13.0% | | |
| Hexanes | | 3.0% | |
| Hexenes | 3.0% | | |
| Heptanes | | 2.0% | |
| Benzene | | | 0.5% |
| Toluene | | | 0.8% |
| Xylene | | | 0.8% |
| Total | 89% | 9% | 2% |

Data from table 2 above clearly indicate the high selectivity of desired olefin using TS-1 as the catalyst which results in a feed composition suitable to alkylate production.

Figure 5:
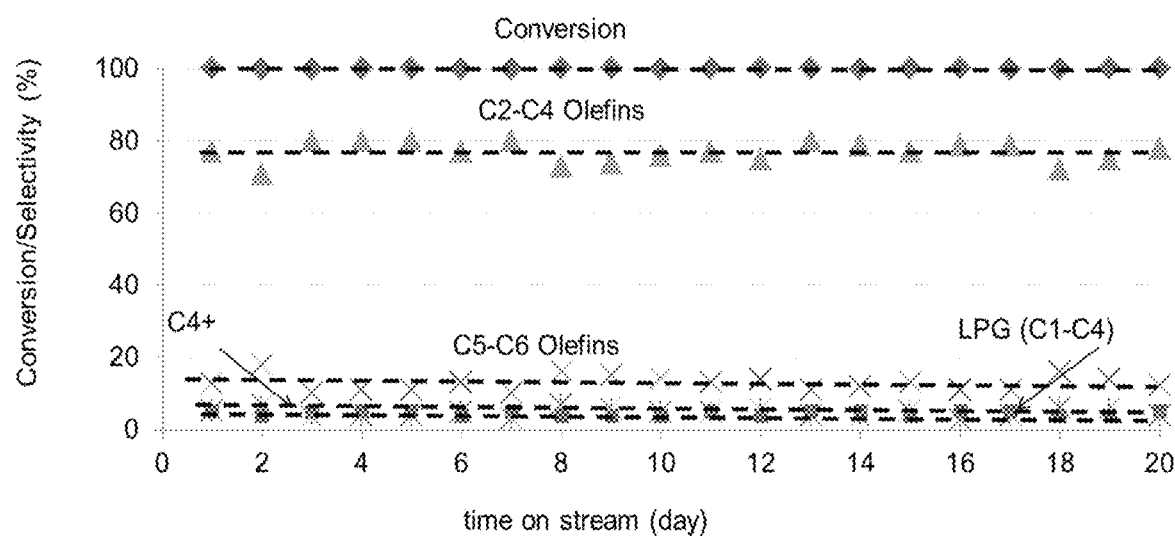
FIG. 5. Long term stability test for conversion of DME to light olefins over TS-1 catalyst
FIG. 6. Fixed-bed recycle reactor test unit for alkylating iso-butane with light olefins

12 Catalyst A titanium silicalite TS1 from ACS Material, Medford, Mass.) was used for a long term stability test. Experiments were performed using an isothermal packed bed reactor setup. Heating was controlled using an Omega temperature control unit and a ceramic heating element. The catalyst (5 gm) was first loaded into a reactor shown in FIG. 3, a center thermocouple (K-type) was inserted and positioned such that the tip of the thermocouple (3.1 mm diameter) was at the bottom of the catalyst bed. 1 mm glass beads were used to fill any void space in the reactor. The catalyst was activated in dry air at atmospheric pressure at 475° C. (4 hours). Following activation the reactor was then purged with dry nitrogen for 0.5 hours. DME was fed at 5 gm/hr using a mass flow controller. The reaction was then conducted at 475° C., WHSV (weight hourly space velocity)=1.0 l/hr and atmospheric pressure. After 8 hours, the DME flow was stopped and the catalyst regenerated in flowing air at 475° C. for 4 hrs. After regeneration was complete, the DME flow was re-started. The products were analyzed using a HP5890 GC equipped with a Petrocol DH column. The results are shown below. The DME conversion remained 100% for the entire duration of the test while olefin selectivity remained constant at >85 wt %. FIG. 5. shows the results for long term stability testing for conversion of DME to light olefins over TS-1 catalyst.

13 Catalyst A titanium silicate TS1 and Catalyst B, titanium silicate impregnated with nickel and zinc, were used for the combined test. Experiments were performed using an isothermal packed bed reactor setup shown in FIG. 4. 5 gm Catalyst A mixed with glass beads were first loaded into the reactor followed by 5 gm of Catalyst B mixed with additional glass beads loaded into the same reactor. Glass beads were added to fill any void space.

The catalyst was activated in dry air at atmospheric pressure at a GHSV of approximately 1000 hr$^{-1}$. The temperature program used to activate the catalyst is: 80° C. (1 hour), 120° C. (1 hr), 230° C. (2 hours), 475° C. (at least 4 hours). Following activation the reactor is purged with dry nitrogen for 0.5 hours.

The reaction was conducted at 475° C. and atmospheric pressure. A mixture of iso-butane and DME were fed to the reactor at a WHSV of 1.0 l/hr. The products were analyzed using a HP5890 GC equipped with a Petrocol DH column.

The results for the combined test are shown below.

TABLE 4

Performance of coupled iso-butane dehydrogenation reaction with DME conversion to light olefins ($C_2$-$C_6$) over TS-1 and Ni-Zn/TS-1 catalyst bed

| Parameter | Results |
| --- | --- |
| DME conversion (%) | 100% |
| Olefin Selectivity (%) | 81 wt % |
| Paraffin Selectivity (%) | 15 wt % |
| BTX Selectivity (%) | 3 wt % |
| Product Iso-butane to Olefin Ratio (mole/mole) | 10 |

The test clearly shows the benefit of using staged catalyst beds to produce a reactor effluent that is suitable as feed for producing alkylate using solid or liquid acid catalysts.

Figure 6:
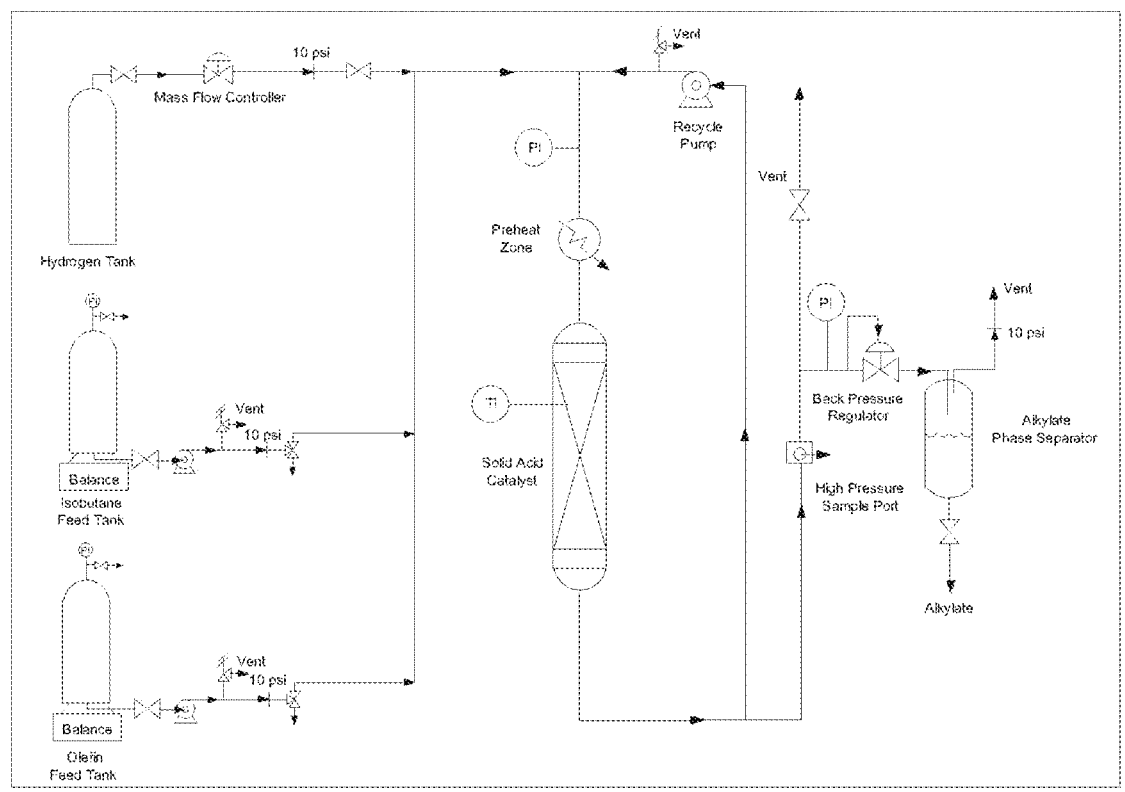

14. Alkylation activity experiments were performed using an isothermal packed bed reactor with product recycle as shown in FIG. 6. Heating is controlled using an Omega temperature control unit and a ceramic heating element. Feeds are sent through a preheater of ~75 cm length prior to entering the reactor.

The catalyst K (10 g) is first loaded into a reactor shown in FIG. 6 (7.9 mm diameter), a center thermocouple (K-type) is inserted and positioned such that the tip of the thermocouple (3.1 mm diameter) is at the bottom of the catalyst bed. 1 mm glass beads are used to fill any void space in the reactor. The catalyst is deaminated in dry air (GHSV=1000 hr-1) at atmospheric pressure using the following temperature program: 100° C. (0.5 hour), 120° C. (1 hour), 230° C. (2 hours), 400° C. (4 hours). Following deamination the reactor is allowed to cool to reaction temperature (45° C.), then purged with dry nitrogen (GHSV=1000 hr-1) for 0.5 hours. The reactor is pressurized (300 psig) with pure isobutane to begin the experiment.

The reaction feed is contained in helium-purged Hoke cylinders. Isobutane and light olefins (composition shown above) were fed to the reactor using an Eldex HPLC pump All feed and product analysis uses this GC system with the following program: 60° C. (16 min), ramp at 15° C./min to 245° C. and soak (20 min).

The experiment is run using an olefin hourly space velocity equal to 0.1 hr-1 and a feed I/O ratio of ~10 with an olefin distribution that models the feed effluent from example 13. Product samples are extracted using a high pressure sampling port and syringe (Vici Precision Sampling) and immediately injected into the HP5890 GC for analysis.

TABLE 5

Alkylate Product Composition for alkylating iso-butane with olefins produced by coupling iso-butane dehydrogenation/cracking with DME to olefins reaction

| Component | Concentration (wt %) |
| --- | --- |
| Iso-pentane | 7.06% |
| n-pentane | 0.00% |
| 2,2-dimethylbutane | 0.81% |
| 2,3-dimethylbutane | 0.00% |
| 2-methylpentane | 0.00% |
| 3-methylpentane | 0.74% |
| 2,4-dimethylpentane | 3.46% |
| 2,2,3-trimethylbutane | 0.22% |
| 2-methylhexane | 0.00% |
| 2,2-dimethylpentane | 0.22% |
| 2,3-dimethylpentane | 6.4% |
| 3-methylhexane | 0.22% |
| 2,2,4-trimethylpentane | 20.22% |
| Unknown C8 | 0.25% |
| 2,2 dimethylhexane | 0.00% |
| 2,5 dimethylhexane | 0.88% |
| 2,4 dimethylhexane | 2.28% |
| 2,2,3-trimethylpentane | 4.63% |
| 2,3,4-trimethylpentane | 13.24% |
| 2,3,3-trimethylpentane | 21.4% |
| 2,3 dimethylhexane | 1.62% |
| 2-methylheptane | 0.44% |
| 3,4-dimethylhexane | 2.57% |
| 3-methylheptane | 0.22% |
| 3,3-dimethylhexane | 0.22% |
| 2,2,5-trimethylhexane | 1.25% |
| C9+ | 11.32% |

| Alkylate Properties: | |
| --- | --- |
| Reid Vapor Pressure: | 3.82 psi |
| Specific Gravity: | 0.7 |
| RON: | 95 |
| MON: | 92 |
| Yield (vol/vol olefin) | 1.85 |

The product distribution is shown in table 5. The olefin conversion remains at 100% for 24 hrs while the RON and MON numbers level off to 95 and 92.

Table 6 shows the near absence of aromatics in the alkylate for the Exelus process as well as a significant increase in MON rating—a jump of over 8 points. The results obtained are compared to a conventional MTG process (Methanol to Gasoline Technology Presentation, GTL Technology Forum 2014, Houston, Tex., (July 2014).

TABLE 6

Product Composition for Exxon MTG process compared to the Exelus methanol/butanes to alkylate process

| Product Distribution, wt. % | MTG | Exelus M2Alk |
|---|---|---|
| LPG (C1-C4) | 23 | 2 |
| C5+ Distribution | | |
| Alkylate | | 96 (iso) |
| Naphtha (C5-C9) | 56 | |
| Aromatics | | 2 |
| Benzene | <0.1 | |
| Toluene | 1 | |
| Xylene | 6 | |
| TriMethylBenzene | 7 | |
| TetraMethylBenzene | 7 | |
| RON | 92 | 95 |
| MON | 82 | 92 |
| Reid Vapor Pressure, psi | 12.3 | 3.82 |
| Density, kg/L | 0.73 | 0.7 |

What is claimed is:

1. A staged reactor system for the synthesis of light olefins, comprising:
   a reactor comprising plural alternating first and second zones in a series of at least two first zones alternating with at least two second zones; and
   a flow path through the series of plural alternating first and second zones;
   wherein the first zones comprise a first catalyst and an inlet for methanol or DME;
   wherein the first catalyst comprises a crystalline Si/Ti zeotype material in which tetrahedral [$TiO_4$] and [$SiO_4$] units are arranged in a MFI structure with a three-dimensional system of channels having a molecular dimension of 4.9 to 5.9 Å, and at least 0.5 mass % Ti;
   wherein the second zones comprise a dehydrogenation or cracking second catalyst;
   wherein the first and second catalysts are different.

2. The staged reactor system of claim 1 comprising butane in the flow path and DME in the first zones.

3. The staged reactor system of claim 2 wherein the dehydrogenation second catalyst comprises at least 1, wt % with an upper bound of 25, or 20 wt % of Pt, Pd, Nickel, Cobalt, Copper, Zinc, Iron, Ru, Rh, Sn, or combinations thereof.

4. The staged reactor system of claim 3 where the second catalyst comprises a catalyst support comprising carbon, SiO2, $Al_2O_3$, TiO2, ZrO2, CeO2, $Y_2O_3$, Silica-Alumina, Zeolite Y, Zeolite USY, Zeolite ZSM-5, TS-1, Zeolite Beta, Zeolite Mordenite or combinations thereof.

5. The staged reactor system of claim 2 comprising multiple beds of the first catalyst and wherein DME is fed into the each of the multiple beds.

6. The staged reactor system of claim 1 wherein the dehydrogenation second catalyst comprises at least 2, or at least 5 wt %, or any of these minimum amounts with an upper bound of 20, or 15, or 10 wt % of Pt, Pd, Nickel, Cobalt, Copper, Zinc, Iron, Ru, Rh, Sn, or combinations thereof.

7. The staged reactor system of claim 6 where the second catalyst comprises a catalyst support comprising carbon, SiO2, $Al_2O_3$, TiO2, ZrO2, CeO2, $Y_2O_3$, Silica-Alumina, Zeolite Y, Zeolite USY, Zeolite ZSM-5, TS-1, Zeolite Beta, Zeolite Mordenite or combinations thereof.

8. The staged reactor system of claim 1 wherein the first catalyst comprises a crystalline zeotype material in which tetrahedral [$TiO_4$] and [$SiO_4$] units are arranged in a MFI structure with a three-dimensional system of channels having a molecular dimension of 5.1-5.6 Å.

9. The staged reactor system of claim 8 wherein the catalyst comprises at least 1% Ti.

10. The staged reactor system of claim 9 wherein the crystalline zeotype material comprises TS-1.

11. The staged reactor system of claim 9 wherein the catalyst contains at least 20 mass % TS-1.

12. The staged reactor system of claim 9 wherein the reactor system comprises a fixed bed reactor.

13. The staged reactor system of claim 8 wherein the catalyst comprises 1 to 5 mass % Ti.

* * * * *